US009440760B2

(12) United States Patent
Srnka et al.

(10) Patent No.: US 9,440,760 B2
(45) Date of Patent: *Sep. 13, 2016

(54) METHOD AND APPARATUS FOR PRINTING LABELS FOR MEDICAL APPLICATIONS

(71) Applicant: Codonics, Inc., Middleburg Heights, OH (US)

(72) Inventors: Lawrence Srnka, Northfield Center, OH (US); Peter Botten, Lakewood, OH (US)

(73) Assignee: CODONICS, INC., Middleburg Heights, OH (US)

( * ) Notice: Subject to any disclaimer, the term of this patent is extended or adjusted under 35 U.S.C. 154(b) by 82 days.

This patent is subject to a terminal disclaimer.

(21) Appl. No.: 14/075,337

(22) Filed: Nov. 8, 2013

(65) Prior Publication Data

US 2014/0060729 A1 Mar. 6, 2014

Related U.S. Application Data

(63) Continuation of application No. 12/901,088, filed on Oct. 8, 2010, now Pat. No. 8,582,171.

(51) Int. Cl.
*G06K 15/00* (2006.01)
*G06F 3/12* (2006.01)
*B65C 9/46* (2006.01)
*G09F 3/10* (2006.01)
*A61L 2/00* (2006.01)

(52) U.S. Cl.
CPC .............. *B65C 9/46* (2013.01); *G06F 3/1208* (2013.01); *G06F 3/1264* (2013.01); *G06F 3/1271* (2013.01); *G06F 3/1284* (2013.01); *G09F 3/10* (2013.01); *A61L 2/00* (2013.01); *Y10T 156/1052* (2015.01)

(58) Field of Classification Search
CPC ...... B65C 9/46; G06F 3/1264; G06F 3/1284; G06F 3/1271; G06F 3/1208; G09F 3/10; Y10T 156/1052; A61L 2/00
USPC ............................ 283/900, 901, 81; 235/494
See application file for complete search history.

(56) References Cited

U.S. PATENT DOCUMENTS

| 7,344,671 B2 * | 3/2008 | Basque ................ B23K 26/032 156/251 |
| 2005/0079096 A1 * | 4/2005 | Brown-Skrobot ........ A61L 2/10 422/24 |
| 2006/0221363 A1 * | 10/2006 | Roth .......................... B41J 3/36 358/1.6 |
| 2007/0244005 A1 * | 10/2007 | Roth .......................... G09F 3/10 503/226 |
| 2008/0116106 A1 * | 5/2008 | Lampropoulos ....... A45C 11/24 206/570 |
| 2008/0141888 A1 * | 6/2008 | Haas ...................... G09F 3/0294 101/491 |
| 2009/0114729 A1 * | 5/2009 | Conner ..................... A61L 2/28 235/494 |
| 2009/0230179 A1 * | 9/2009 | Livolsi .................. G06F 19/327 235/375 |
| 2011/0067781 A1 * | 3/2011 | Osborne ................. B65B 3/003 141/37 |

FOREIGN PATENT DOCUMENTS

WO    WO 2009147252 A1 * 12/2009  ............. B65B 3/003

* cited by examiner

*Primary Examiner* — Dov Popovici
(74) *Attorney, Agent, or Firm* — Pearne & Gordon LLP

(57) ABSTRACT

Provided is a method and apparatus for generating a label for use in a medical application. Label content specified by a user that is to be applied to a surface of the label is received. The label content, which includes a machine-generated character, is printed on demand onto the surface of the label. The label bearing the label content is dispensed in a condition suitable for use in the sterile environment.

16 Claims, 4 Drawing Sheets

METHOD AND APPARATUS FOR PRINTING LABELS FOR MEDICAL APPLICATIONS

CROSS-REFERENCE TO RELATED APPLICATIONS

This application is a continuation of application Ser. No. 12/901,088, filed Oct. 8, 2010, which is incorporated in its entirety herein by reference.

BACKGROUND OF THE INVENTION

1. Field of the Invention

This application relates generally to printing labels and, more specifically, to a method and apparatus for printing substantially-sterile labels for labeling objects in medical applications.

2. Description of Related Art

Sterile environments are common in the medical field for treating patients with minimal risk of infection. To avoid exposing patients in such environments to infectious organisms medical personnel working therein are required to take precautionary measures. All personnel are required to wash thoroughly before entering the environment, and wear items of clothing such as surgical scrubs that have been decontaminated.

Other objects such as medical equipment can also be contaminated with infectious organisms and such organisms into sterile environments. Bedding, medical devices, and virtually all other objects brought into a sterile environment must undergo sterilization procedures to minimize the risk of infection to patients. Labels for identifying medications, personal possessions, tissue samples, or any other object within a sterile environment are among the other objects that also undergo a sterilization procedure.

Traditionally, each label has been sterilized by the manufacturer before being sealed within an individual wrapper before the wrapped labels were distributed to users. Likewise, pens used for hand writing label content on sterile labels have also been sterilized by the manufacturers and sealed in individual wrappers to be distributed to users in the medical field. In use, a wrapped label would be retrieved from a bin of such labels along with a wrapped pen. Both the label and the pen were opened by the user within or near the sterile environment, and the label content applied to the sterile label with the sterile pen. However, this traditional method and system for providing sterile labels in the medical field is prone to errors due to illegible handwriting.

BRIEF SUMMARY

Accordingly, there is a need in the art for a method and apparatus for generating a machine-printed, substantially-sterile label on demand for use in medical applications.

According to one aspect, the subject application involves a method of generating a label for use in a medical application. The method includes receiving label content specified by a user that is to be applied to a surface of the label. The label content comprising a machine-generated character is printed, on demand, onto the label, and the label bearing the label content is dispensed in a substantially-sterile condition for use in the medical application.

According to another aspect, the subject application involves a printer for generating a label for use in a medical application. The printer includes a label feeder that supplies labels on which label content is to be printed, and a print head that applies the label content comprising a machine-generated character to the label on demand. A dispenser that dispenses the label bearing the label content in a substantially-sterile condition for use in the medical application is also provided.

According to another aspect, the subject application involves a printer accessory that is to cooperate with a printer for producing labels for use in a medical application. The printer accessory includes a receiver for receiving the label with label content printed, on demand and at a facility where the label is to be used in the medical application, and dispensed by the printer. The label content includes machine-generated characters. A packager that introduces the label with the label content to a package that is to at least partially enclose the label and dispenses the label in a substantially-sterile condition suitable for use in the medical application is also provided.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

DETAILED DESCRIPTION

Figure 1:
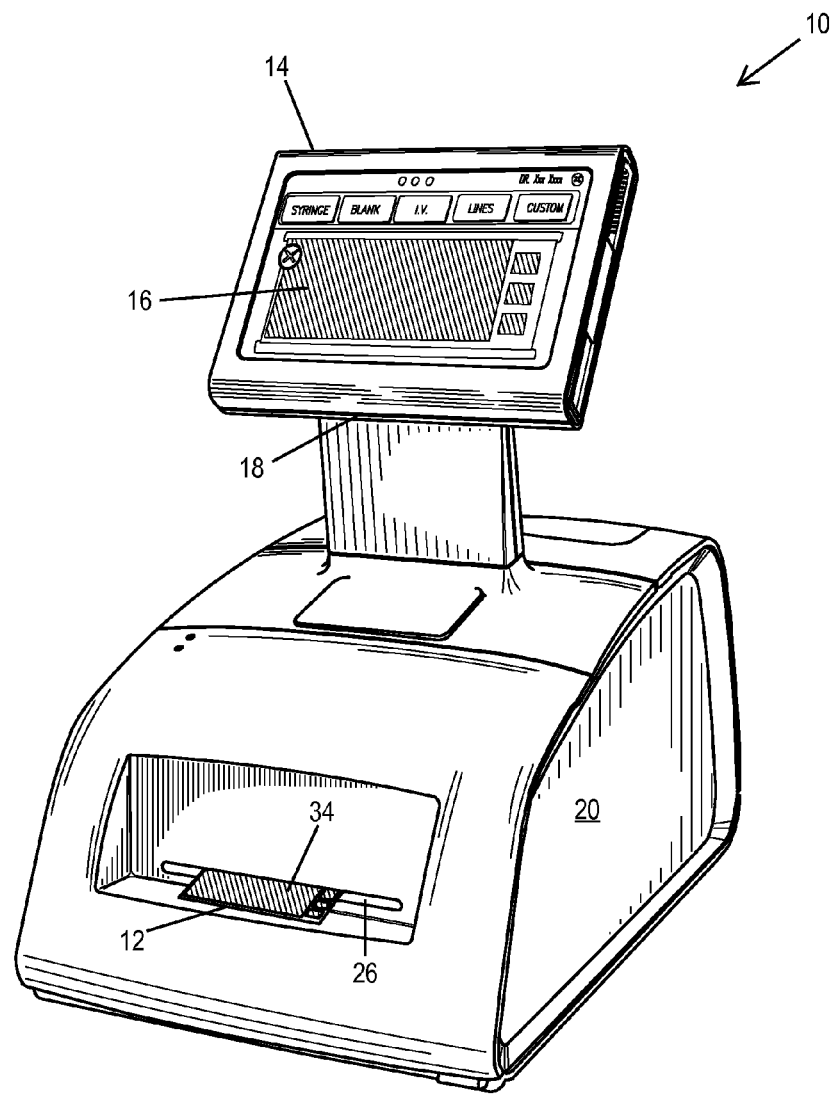
FIG. 1 shows an illustrative embodiment of a computer-controlled printer for producing, on demand, a label in a substantially-sterile condition.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

It is also to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

FIG. 1 shows an illustrative embodiment of a computer terminal 10 including an integrated printer 26 for generating a label 12 to be used for labeling purposes in a healthcare, medical or life science application (referred to generally herein as a "medical application"). For embodiments where the labels 12 are to be used in a medical application, the printer 26 can optionally be configured to print a machine-readable code on the label 12 to facilitate record keeping with respect to the object on which the label 12 is to be applied. The machine-readable code printed by the printer 26 can streamline the entry of the information into a computer network such as a Hospital Information System ("HIS") and/or a Radiology Information System ("RIS"), for example. However, the description below also encompasses any conventional computer printer, including those that are computer peripherals to a conventional general-purpose computer. The label 12 is to be used in any medical application such as identifying a medicinal substance to be administered to a patient, labeling a medical device in a healthcare facility, and labeling any other object encountered in the healthcare, medical or life science fields with any type of information, for example. However, for the sake of brevity, the generation of a label in a substantially-sterile condition for labeling a medicinal substance such as a medication to be administered to a patient is described in the examples below.

As shown in FIG. 1, the computer terminal 10 includes a touch-screen display 14 that displays a virtual label 16 to be printed as the label 12, and displays soft keys that can be touched by a technician or any user to input data and commands into the computer terminal 10. The virtual label 16 is a computer-generated rendering of the label 12 that offers the user visual confirmation of the appearance of the physical label 12 to be printed by a printer 26. A computer-input peripheral such as a contactless scanner 18 can be provided at a convenient location such as adjacent a bottom portion of the display 14 to read a machine-readable code. For example, the computer-input peripheral can be a barcode reader or radio-frequency identification ("RFID") tag reader, or any other device that reads a machine-readable code such as a barcode or RFID code, respectively, or any other machine-readable code, with or without requiring contact between the computer terminal and the code, and optionally without requiring additional input from the user during entry of the code. Alternate embodiments can include a scanner 18 that can not only read the machine-readable code, but also transmit data to programmable embodiments of the code such as a RFID tag. According to yet alternate embodiments, the display 14 can be utilized by a user as the computer-input peripheral. For such embodiments, the soft keys displayed by the display 14 can be selected to input information such as a medicinal substance being prepared to be administered to a patient or other information to be utilized in generating the label as described herein.

The computer terminal 10 also includes a cabinet 20 housing components that are operable to produce the label 12 in a substantially-sterilized condition. The label can also optionally be compliant with a medical labeling standard addressing the content, format, arrangement, any other aspect of labels 12 to be employed in the medical field, or any combination thereof. The cabinet 20 can also support the display 14 and the scanner 18 to form a self-contained, stand-alone unit. The internal components housed within the cabinet 20 are schematically illustrated by the block diagram of FIG. 2. A computer processor 22 is provided to execute computer-executable instructions stored in a non-transitory computer readable memory 24 such as a hard disk drive, read-only memory ("ROM"), random access memory ("RAM"), optical disc, or any other suitable memory device. The computer-executed instructions, when executed by the computer processor 22, result in the performance of the method of generating a label for a medicinal substance described in detail below. A bus system 28 facilitates communication between components such as the display 14, scanner 18, processor 22, memory 24 and printer 26.

The printer 26 includes a print head 30 for applying label content comprising at least one machine-generated character to the label 12, on demand, delivered to the print head 30 by a feeder 32 of label stock. The print head 30 can fall within any category of printing technology suitable to apply label content onto label stock. For example, the print head 30 can be an inkjet print head that deposits droplets of ink in a pattern to create the label content, a thermal print head that applies label content through application of a thermal printing process, a laser print head that directs a laser across a photoreceptor to create the pattern for the label content to be printed, a solid-ink print head, a dot matrix print head, and the like.

The feeder 32 can be adapted to support a roll of label stock that has base labels supported on a release tape, can include a tray for storing a supply of individual base labels, or any other source of labels on which label content is to be printed. The feeder 32 can be internally disposed within the printer 26 or located at an external location relative to the printer 26 from where it can feed base labels into the printer 26.

The computer terminal 10 can be deployed at a healthcare facility such as a hospital or surgical center, or anywhere a substantially-sterile label 12 is desired to minimize the risk of infection to a living organism, for example. An operating room, treatment room, or other substantially-sterile environment such can optionally be provided within the healthcare facility, and the printer 26 disposed within, or immediately adjacent to such a substantially-sterile environment. According to such embodiments, the label 12 can optionally be generated as described in detail below within, or at least within a close proximity to the substantially-sterile environment, or elsewhere the same facility where the label 12 is to be used.

For the illustrative embodiment of the label 12 shown in FIG. 1, the label content is applied by the printer 26 on a content surface 34 of the label 12 that is exposed and viewable by observers when the label 12 is applied to a syringe or other container storing the medicinal substance. An adhesive surface (opposite the content surface 34) can also be provided to be applied against a syringe, other container or any other object to adhere the label 12 to such objects.

The label content can include any identifying or other desired information about the object to be labeled, and is printed on-demand by the computer printer 26 under the control of one or more users who are involved in labeling the medicinal substance or other object in the medical field, or their agents. By "on demand" it is meant that the label is caused to be generated by the aforementioned users at a moment when the label 12 is desired. That moment can be when the label 12 is to be used for labeling purposes, such as when the label 12 is desired to be placed on a syringe storing a medicinal substance or while the syringe is being prepared, for example, or as needed at any other time prior to use of the label in the sterile environment. According to an alternate embodiment, the label 12 can be printed at a time when the syringe or other container is being prepared with the medicinal substance to be labeled, or shortly before or after preparation of the syringe or other container with the medicinal substance to be labeled.

Figure 2:
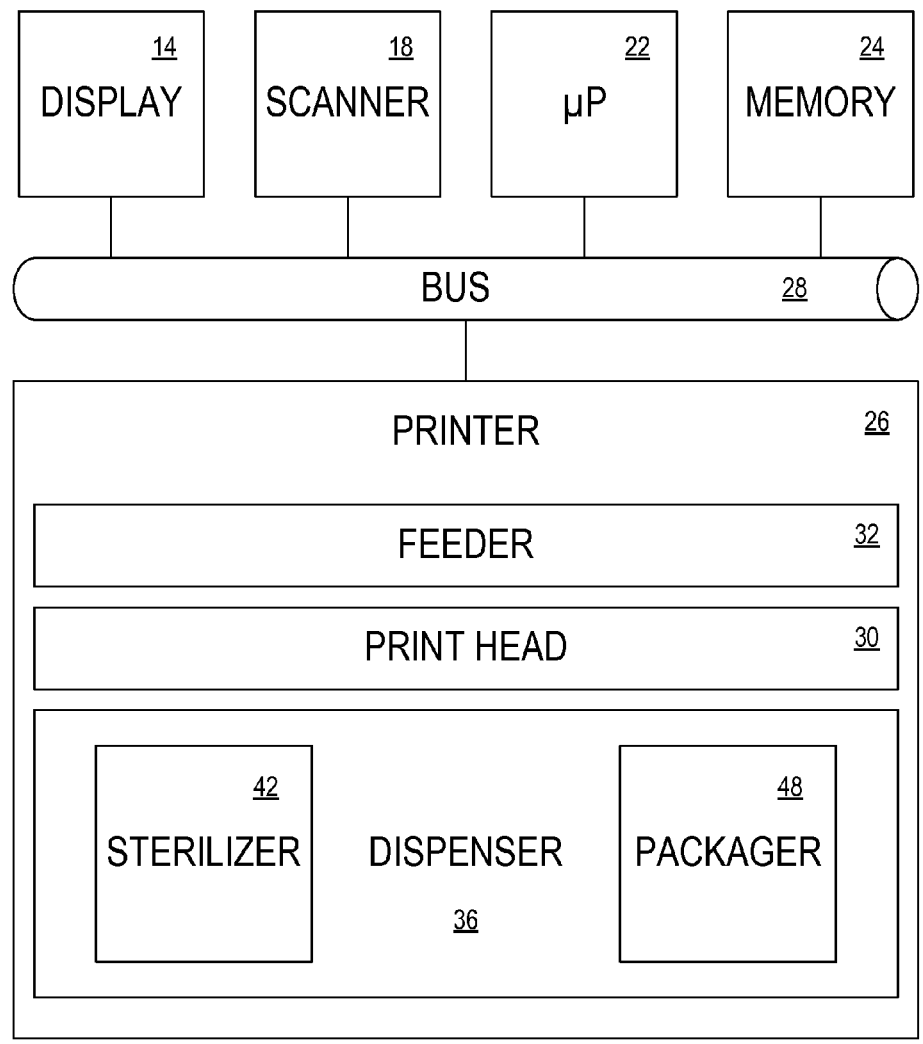
FIG. 2 shows a block diagram illustrating components of the computer terminal shown in FIG. 1.

The embodiment of the printer 26 in FIG. 2 also includes a dispenser 36 that dispenses the label 12 bearing label content in a substantially-sterile condition for use in the medical application. For a label 12 to be in a substantially-sterile condition, at least one of the following mush occur: a portion, and optionally the entire label 12 must have undergone a sterilization procedure; a portion, or optionally all of a package 38 (FIGS. 3 and 4) that is to least partially enclose the label 12 must have undergone a sterilization procedure; or a combination thereof. For example, the content surface 34 or other portion of the label 12 can be exposed to a sterilizing agent that can kill a substantial portion of any living organisms on the content surface 34. Examples of suitable sterilizing agents include, but are not limited to UV light, liquid or dry chemical disinfectants, steam, radiation, etc. . . . . The sterilization procedure can optionally be performed by the dispenser 36 provided to the printer 26, or by another party such as a manufacturer of label stock before the label stock is provided to the feeder 32 of the printer.

Figure 3:
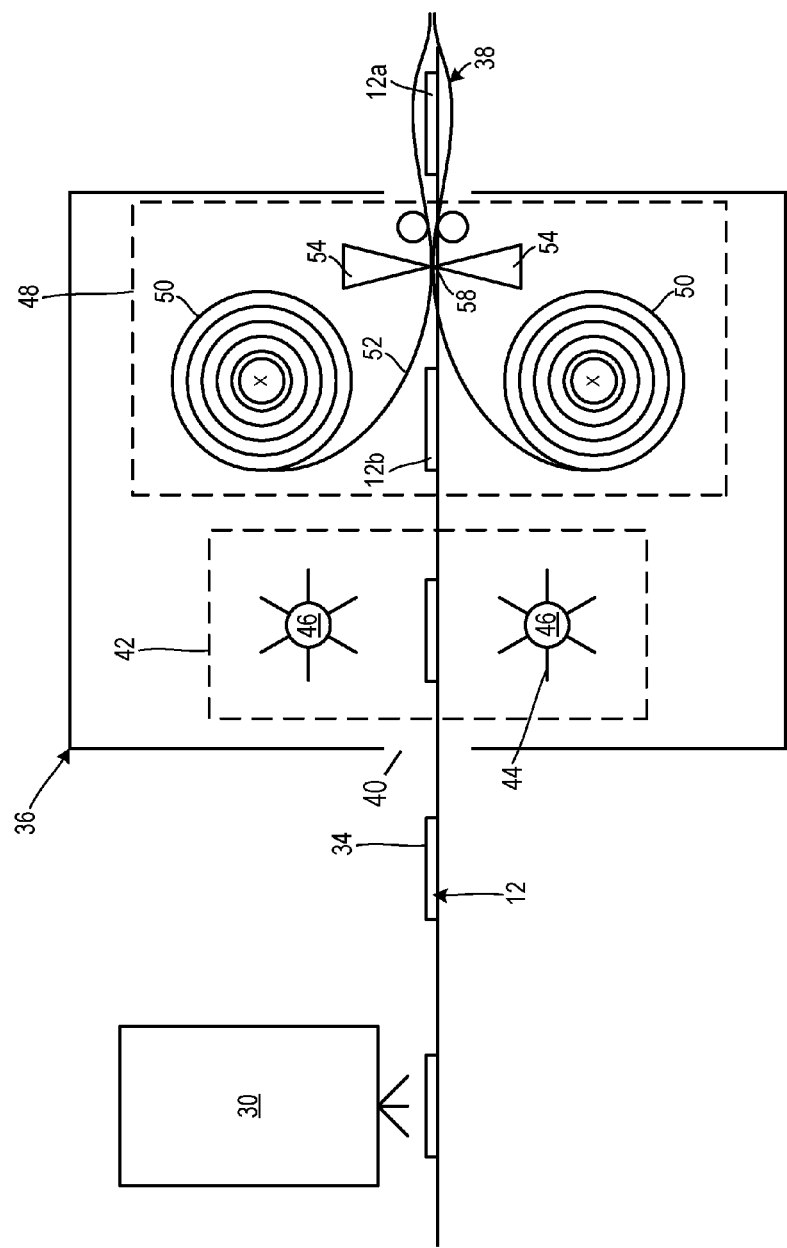
FIG. 3 shows an illustrative embodiment of a dispenser provided to a printer for dispensing labels in a substantially-sterile condition.

An embodiment of a dispenser 36 is shown schematically in FIG. 3. As shown, the dispenser is provided to a printer 26 as an after market peripheral, connected to receive labels 12 bearing label content printed by an inkjet print head 30. The labels 12 are received by the dispenser 36 through a receiver 40, which in the embodiment shown in FIG. 3 is an aperture through which the labels 12 enter the dispenser 36.

Once the labels 12 have had the label content printed thereon and have been received by the dispenser 36, those labels 12 are introduced to a sterilizer 42, which exposes at least the content surface 34 of the labels 12 to a sterilizing agent. In the embodiment shown in FIG. 3, the sterilizing agent is UV light 44 emitted from an UV illumination source 46. Further, according to the present embodiment a plurality of UV illumination sources 46 are provided on opposite sides of the labels 12 being subjected to the sterilization procedure. Such an arrangement allows for substantial sterilization of opposite sides of the label 12.

From the sterilizer 42 the labels 12 are subsequently introduced to a packager 48, identified by broken lines. The packager 48 introduces the labels 12 to a package material that at least partially encloses the labels 12. According to the embodiment illustrated in FIG. 3, the packager 48 includes two rolls 50 of a non-sterile plastic film 52. Of course materials other than plastic can be used for the film 52, which can also be supplied in forms other than rolls 50. A segment of the film 52 is placed over the content surface 34 of the labels 12 and another segment of film from the other roll 50 under the opposite planar surface of the label 12 relative to the segment passing over the label 12. The film 52 can be subjected to the sterilizing procedure, or can be formed from a material that is not subjected to a sterilization procedure and, thus, is in a substantially-sterilized condition. For example, the inward-facing surface of each film 52 that is to face the label 12 when formed into the package 38 is exposed to the UV light 44 from the UV illumination source 46. For embodiments where the films 52 are substantially (or at least partially) transparent, this UV light 44 can optionally be transmitted through the films 52 to also substantially sterilize the other outward-facing major surface of one or both films 52. Yet other embodiments of the dispenser 36 can include one or a plurality of additional UV illumination sources (instead of, or in addition to the UV illumination sources 46) disposed adjacent to the outward-facing surface of one or both films 52 to expose those outward-facing surfaces to the UV light 44 to substantially sterilize those outward facing surfaces. The outward-facing surface of each film 52 faces away from the label 12 when formed into the package 38.

A pair of adjustable heat stakes 54, or any other suitable device for coupling the film 52 from the different rolls 50 together, is used to seal the package 38 formed by the films 52 at opposite ends of the label 12. For the example shown in FIG. 3, the heat stakes 54 are brought together to pinch the films together at the pinch point 58. At least the pinching ends of one or both of the stakes that contact the films 52 is heated to a suitable elevated temperature to melt the films 52 together at the pinch point 58. The location where the films 52 are being joined together by the heat stakes 54 in FIG. 3 seals the package 38 enclosing the substantially-sterile label 12a being dispensed from the dispenser 36 and establishes the first seal of the package that is to at least partially enclose the next substantially-sterile label 12b. The heat and pressure from the heat stakes 54 can also optionally separate the substantially-sterile label 12a from the next substantially-sterile label 12b.

To apply the substantially-sterile label 12a to an object to be labeled, the user can retrieve the substantially-sterile label 12a being dispensed and peel the segments of films 52 that collectively form the package 38 away from each other. A release liner against which the adhesive surface of the substantially-sterile label 12a is applied can be removed and the substantially-sterile label 12a adhered to the object to be labeled.

In use, the printer 26 receives label content specified by a user. The user can specify the label content by keying the label content into the computer 10 using a keyboard or soft keys presented on the display 14, scanning a machine-readable code using the scanner 18, or in any other manner. Upon receiving the label content, the printer 26 can, on demand, and optionally automatically without user intervention in response to receiving the label content, print the label content on the label 12.

Between packaging the label 12 and printing the label content, the label 12, or at least a portion thereof, is exposed to the UV light 44 to place the label 12 in a substantially-sterile condition. Following exposure to the UV light 44 the label 12 is packaged between the plastic films 52, one from each roller 50. The heat stakes 54 come together and are heated, thereby completing the enclosure of the label 12 and separating the label 12 from others being dispensed.

Figure 4:
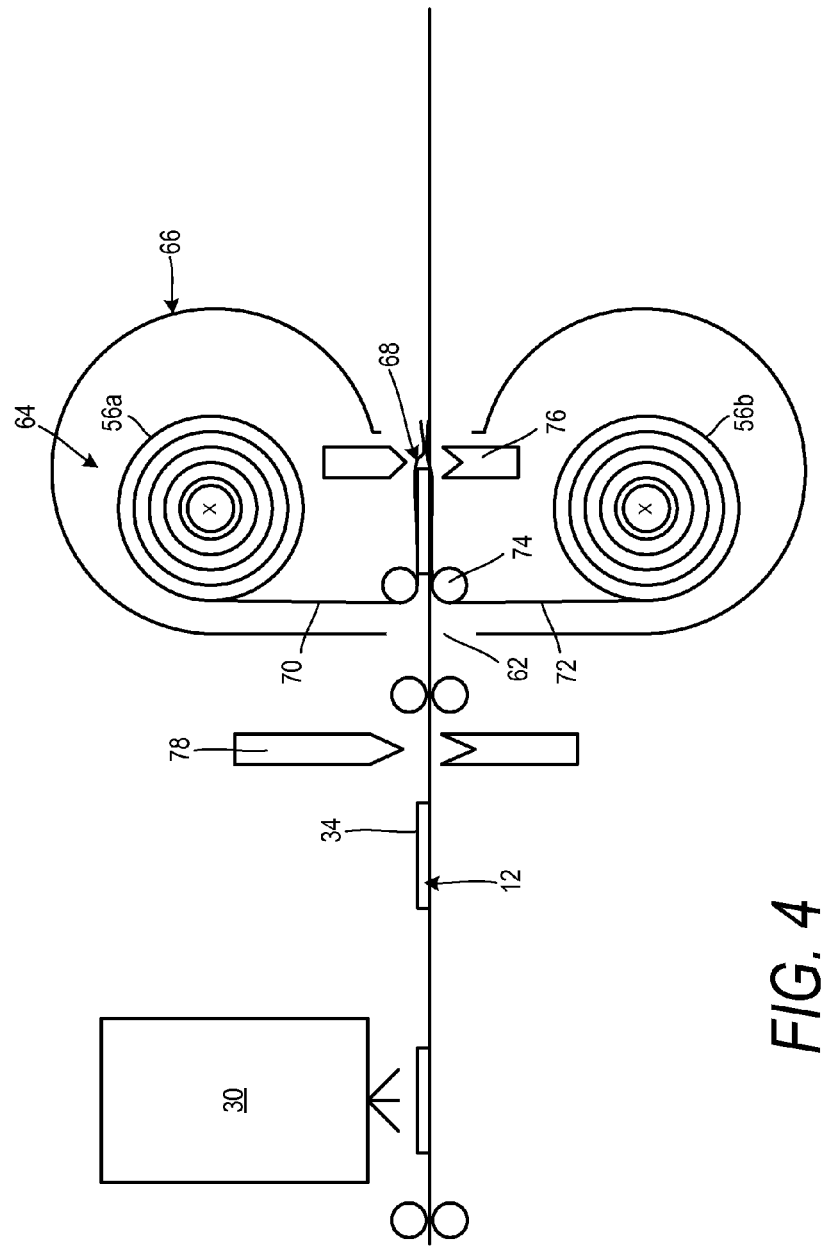
FIG. 4 shows another illustrative embodiment of a dispenser provided to a printer for dispensing labels in a substantially-sterile condition.

Another illustrative embodiment of a dispenser 66 is schematically illustrated in FIG. 4. Like the embodiment shown in FIG. 3, the present embodiment includes a receiver 62 in the form of an aperture through which labels 12 with label content already printed thereon by the print head 30 can enter the dispenser 66.

Also similar to the embodiment shown in FIG. 3, the present embodiment also includes a packager 64 comprising two rolls 56a, 56b of material that collectively form a package 68 around the labels 12 to be dispensed from the dispenser 66. Unlike the previous embodiment shown in FIG. 4, however, at least one of the rolls 56a, 56b of material is in a substantially-sterile condition, having been previously subjected to a sterilization procedure. Further, the dispenser 66 lacks a sterilizer such as that described with reference to FIG. 3. Instead, the labels 12 are laminated between laminating material 70 from roll 56a and a release layer 72 from roll 56b. The laminating material 70 can be adhesively coupled to the label 12 and or release layer 72, can be heat activated to bond with the release layer and/or label 12 when subjected to heat and pressure, or can be coupled to the release layer in any desired manner to enclose and seal substantially the entire label 12 between the laminating material 70 and release layer 72. Laminating nip rollers 74 can be provided to apply heat and/or pressure against the laminating material 70 and release layer 72 as necessary to seal the package 68 collectively formed thereby.

Labels 12 enclosed within the package are in the substantially-sterile condition because the unsterilized label 12 is substantially entirely, and optionally entirely enclosed by the package 68, which has been subjected to a sterilizing procedure by a manufacturer before being coupled to the printer 26. An optional cutting device 76 can be provided between the laminating nip rollers and the location where the labels 12 in the substantially-sterilized condition are dispensed from the dispenser 66. The cutter 76 is operable to separate the labels 12 from one another to be individually dispensed, each in their own individual package 68. Alternately, an optional cutter 78 can be provided between the print head 30 and the dispenser 66 such that individual labels 12 are received by the dispenser 66 rather than a continuous tape supporting a plurality of labels 12.

According to yet another embodiment, the label 12 on which the label content is to be printed has already been subjected to a sterilization procedure and enclosed within an individual package prior to the printing of the label content. According to such embodiments, the label within the package is introduced to the print head 30, which can be a thermal print head, already packaged and in a substantially-sterile condition. A thermal printing operation is performed with the thermal print head to apply label content onto the label 12 while the label 12 is enclosed within the package. The resulting label bearing the thermally-printed label content and packaged in a substantially-sterile condition is then dispensed for use in the medical field.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method of generating a label for use in a medical application, the method comprising:
   receiving, with a computer-controlled printer having a label supply including a label, label content specified by a user that is to be applied to a surface of the label;
   printing, on demand, the label content comprising a machine-generated character onto the label using a print head;
   after said printing the label content, exposing the label bearing the label content to ultraviolet light to place the label in a sterile condition suitable for use in an operating room during a medical procedure involving a patient; and
   after said exposing the label to the ultraviolet light, dispensing the label bearing the label content in the sterile condition.

2. The method of claim 1 further comprising introducing the label bearing the label content to a package before the label is dispensed, wherein said exposing the label to the ultraviolet light occurs after said printing the label content and before said introducing the label bearing the label content to the package.

3. The method of claim 2, wherein the package comprises a packaging material that is not subjected to a sterilization procedure before being dispensed.

4. The method of claim 3 further comprising sealing an end of the packaging material to fully encapsulate the label in the sterile condition.

5. The method of claim 1, wherein said dispensing the label in the sterile condition suitable for use in the operating room comprises:
   introducing the label bearing the label content to a substantially-sterile package before the label is dispensed; and
   dispensing the label bearing the label content fully enclosed by the substantially-sterile package.

6. The method of claim 5, wherein the package comprises a laminating material applied over a surface of the label and a release liner coupled to the laminating material on an opposite side of the label relative to the laminating material.

7. The method of claim 5 further comprising cutting the substantially-sterile package enclosing the label to a desired length.

8. The method of claim 5, wherein the label is introduced to the package without having been subjected to a sterilization procedure.

9. A printer for generating a label for use in a medical application environment, the printer comprising:
   a label feeder that supplies labels on which label content is to be printed;
   a print head that applies the label content comprising a machine-generated character to the label on demand;
   a dispenser that dispenses the label bearing the label content in a sterile condition suitable for use in an operating room during a medical procedure involving a patient; and
   a UV illumination source provided to the dispenser that emits UV light onto the label bearing the label content to render the label suitable for use in the operating room before the label is dispensed to a user by the dispenser.

10. The printer of claim 9, wherein the dispenser comprises:
    a packager that introduces the label bearing the label content to a package.

11. The printer of claim 10, wherein the packager comprises:
    a feeder that supplies a plastic material to at least partially cover a surface of the label bearing the label content and a substrate that is to extend across a substantial extent of a second surface of the label that is opposite the surface of the label to be viewed to observe the label content; and
    a staking device for staking the plastic material to the substrate to form the package that at least partially encloses the label bearing the label content.

12. The printer of claim 9, wherein the dispenser comprises a packager that introduces the label bearing the label content to a package, said packager comprising a feeder that supplies a laminating material to be placed over a surface of the label and a release liner to be coupled to the laminating material on an opposite surface of the label relative to the laminating material to form the package.

13. The printer of claim 12, wherein at least one of the laminating material and the release liner is in the sterile condition suitable for use in the operating room, having been subjected to a sterilization procedure before being supplied to form the package.

14. The printer of claim 12, wherein the packager further comprises a cutter for cutting the package comprising the laminating material and the release liner, combined.

15. A printer accessory that is to cooperate with a printer for producing labels for use in a medical application, the printer accessory comprising:
- a receiver of a dispenser for receiving a label comprising label content printed, on demand at a medical facility where the label is to be used in the medical application, and dispensed by the printer, said label content comprising machine-generated characters;
- a UV illumination source that emits UV light onto the label bearing the label content; and
- a packager that introduces the label bearing the label content to a package that is to at least partially enclose the label and dispenses the label in a sterile condition suitable for use in an operating room during a medical procedure on a patient, wherein the UV illumination source is disposed between the receiver and the packager.

16. The printer accessory of claim 15, wherein the packager comprises a feeder that supplies a laminating material to be placed over a surface of the label to be viewed for observing the label content and a release liner to be coupled to the laminating material on an opposite side of the label to form the package.

* * * * *